United States Patent

Suzuki et al.

Patent Number: 5,278,295
Date of Patent: Jan. 11, 1994

[54] PYRROLE MONOMER

[75] Inventors: Hirofumi Suzuki; Takehira Kaneko; Nobuo Matsui; Isami Hamamoto, all of Odawara; Tetsuya Katoh, Takaoka; Toshiaki Satoh; Fuminiko Nagasaki, both of Odawara, all of Japan

[73] Assignee: Nippon Soda Co., LTD, Tokyo, Japan

[21] Appl. No.: 848,949

[22] PCT Filed: Oct. 15, 1990

[86] PCT No.: PCT/JP90/01326
§ 371 Date: May 7, 1992
§ 102(e) Date: May 7, 1992

[87] PCT Pub. No.: WO91/05769
PCT Pub. Date: May 2, 1991

[30] Foreign Application Priority Data

Oct. 17, 1989 [JP] Japan ................... 1-268184
Jul. 26, 1990 [JP] Japan ................... 2-196257

[51] Int. Cl.$^5$ ............ C07C 245/08; C09B 29/40; C07D 207/30
[52] U.S. Cl. .................... 534/798; 548/560; 548/561; 548/562; 252/299.61; 252/299.68
[58] Field of Search ........... 548/531, 533, 560, 561; 534/774, 775, 777, 798, 799, 804, 567

[56] References Cited

U.S. PATENT DOCUMENTS

| 3,136,620 | 6/1964 | Bucha et al. ........... 548/531 X |
| 4,129,573 | 12/1978 | Bellus et al. ........... 548/531 |
| 4,342,692 | 8/1982 | Suh et al. ........... 548/531 |
| 5,082,856 | 1/1992 | Taniguchi et al. ........... 548/531 X |

FOREIGN PATENT DOCUMENTS

| 48-28913 | 9/1973 | Japan ........... 548/531 |
| 61-30571 | 2/1986 | Japan ........... 548/531 |
| 62-207324 | 7/1987 | Japan ........... 548/531 |
| 63-22067 | 1/1988 | Japan ........... 548/531 |

OTHER PUBLICATIONS

Lee, J. Amer. Chem. Soc., vol. 88, pp. 3440–3441 (1966).

Primary Examiner—Floyd D. Higel
Attorney, Agent, or Firm—Joseph C. Mason, Jr.; George B. Oujevolk; Ronald E. Smith

[57] ABSTRACT

A pyrrole polymer membrane having electrical conductivity and liquid crystal properties in the same matrix. The starting pyrrole monomer derivative is illustrated by the formula

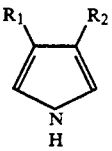

where $R_1$ and $R_2$ are selected so that at least either of them is an electron attractive group. Methods of producing such membranes by a electropolymerization process and by a chemical oxidation process are described.

7 Claims, 7 Drawing Sheets

-40°  40°

-45°  45°

PYRROLE MONOMER

BACKGROUND OF THE INVENTION

The present invention relates to a novel pyrrole monomer, a process for production thereof and to a functional polymer membrane. More particularly, it relates to a conductive polymer membrane having liquid crystal molecules in its side chain.

DESCRIPTION OF RELATED ART

Organic conductive polymers having hetero atoms such as polypyrrole, polythiophene, polyaniline have been subjects of studies different from polyacetylene because the former have stable electrical conductivity in atmospheric conditions. Recently, research efforts have been conducted to bring organic materials to the market of electrical materials, for example, development of secondary batteries having a polyaniline anode, aluminum solid electrolytic condenser having a polypyrrole as an electrolyte. Taking this opportunity, defects of organic materials such as durability, reliability or the like have been gradually reconsidered. Further, investigation of the function of conductive polymer having organic functional molecules (e.g., electronic, electric, optical function etc.) as substituents has been carried out.

It is also known that liquid crystal polymers such as polyamides, polyester, and polyester amides have been studied as an engineered plastic material due to their high strength and high elasticity. Fundamental and development research have been conducted on such polymers as engineering plastics. Further, not only main-chain liquid crystal polymer, but side-chain liquid crystal polymer have been briskly studied. These side-chain polymers have purpose different from that of the main-chain liquid crystal polymer, and may be used as a transducer which can convert change of external information such as light, heat, electricity, strength into different energy utilizing side-chain liquid crystal molecules. For example, application of reversible phase change of liquid crystal corresponding to the change in electric field for liquid crystal display, sensor utilizing change upon heat and the like.

Technique utilizing orientation of polymer liquid crystal for production of conductive polymer film will be shown below.

(1) Conductive polymer film is obtained by adding and by heating polymer liquid crystal and pyrrole monomer and $AlCl_3$ (U.S. Pat. No. 4,772,421).

(2) Conductive polymer film is obtained by adding a photopolymerization initiator to liquid crystal molecules with cross-linking group introduced at the end, and applying electric field to orientate and fixing the orientation (Japanese Patent Laying-Open No. 223906/1987).

(3) The methods for producing conductive film utilizing orientation of previously mixed low-molecular weight liquid crystals are as follows.

(a) Conductive material is obtained by mixing liquid crystal molecules with, for example, molten polyester, followed by cooling and molding the resultant (Ger. Offen. DE 3,613,701).

(b) Liquid crystal molecules, electrolyte, pyrrole are added in a solvent, which is subjected to electrolytic polymerization (Ger. Offen. DE 3,533,242).

However, the method (1), wherein the oriented film of the liquid crystal polymer is previously prepared, and said film is contacted with acetylene or pyrrole, has a defect of requiring a long period of time for polymerization. The method (2) provides very low electrical conductivity (i.e., $6 \times 10^{-7}$ S/cm) due to the deficiency of conjugated double bond chain. In the method (3)(a), it is troublesome to heat polyester to its melting temperature. The method (3)(b) has defect that it required liquid crystal molecule five time the amount of the solvent (37 times the amount of pyrrole).

The present invention provides a novel conductive polymer membrane having two characteristics, i.e., electrical conductivity and liquid crystal property in the same matrix. The present invention also provides a novel pyrrole monomer derivative for the above purpose.

SUMMARY OF THE INVENTION

The present invention relates to a compound represented by the general formula [I]:

{wherein $R_1$ and $R_2$ are selected to that $R_1$ or $R_2$ or $R_1$ and $R_2$ each is an electron attractive group, $R_1$ is hydrogen, cyano, alkyl, phenyl or benzyl which may be substituted, $COR_3$ (wherein $R_3$ means alkyl, phenyl or benzyl which may be substituted) —$COOR_4$ (wherein $R_4$ is hydrogen, alkyl, phenyl or benzyl which may be substituted).

$R_2$ is a group of the formula:

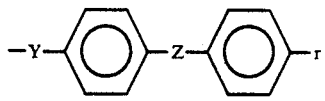

[in which Y is a direct bond, a branched or a straight-chain $C_{1-12}$ alkylene, phenylene, —CO—, —COO—, —COOalk-, —COOalkO—, —COOalkN($R_8$)-(in which $R_8$ is alkyl), or -alkO-(in which alk is a branched or a straightchain $C_{1-12}$ alkylene), Z is —HC≡CH—, —CH=NNH—, —N=N(O)—, —C≡C—, —COO—, —N=N—, —S— or a direct bond, r is hydrogen, nitro, cyano, halogen, alkyl or alkoxy which may have an asymmetric carbon and may be substituted), —$COR_5$ (in which $R_5$ is alkyl which may have an asymmetric carbon and may be substituted, phenyl which may be substituted), —$COOR_6$—, —$OCOR_7$— (in which $R_6$ and $R_7$ are hydrogen, alkyl which may have an asymmetric carbon and may be substituted, phenyl which may be substituted]}, and to a process for production thereof, and to a functional polymer membrane which can be obtained by electropolymerization or chemical oxidation polymerization of a compound of the general formula [I]:

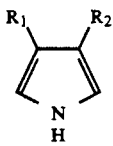

(I)

[wherein $R_1$ and $R_2$ are as defined above],
a mixture of the compounds, or those compounds with pyrrole monomer which does not have a unsubstituted or substituted liquid crystal molecule in its side chain.

In the description of $R_1$ or $R_2$ or $R_1$ and $R_2$ each is an electron attractive group", said electron attractive group means, for example, CN, —CO—, —COO— and the like.

Preparation of Pyrrole Monomer Derivatives

The novel pyrrole monomer of the present invention is produced as follows:

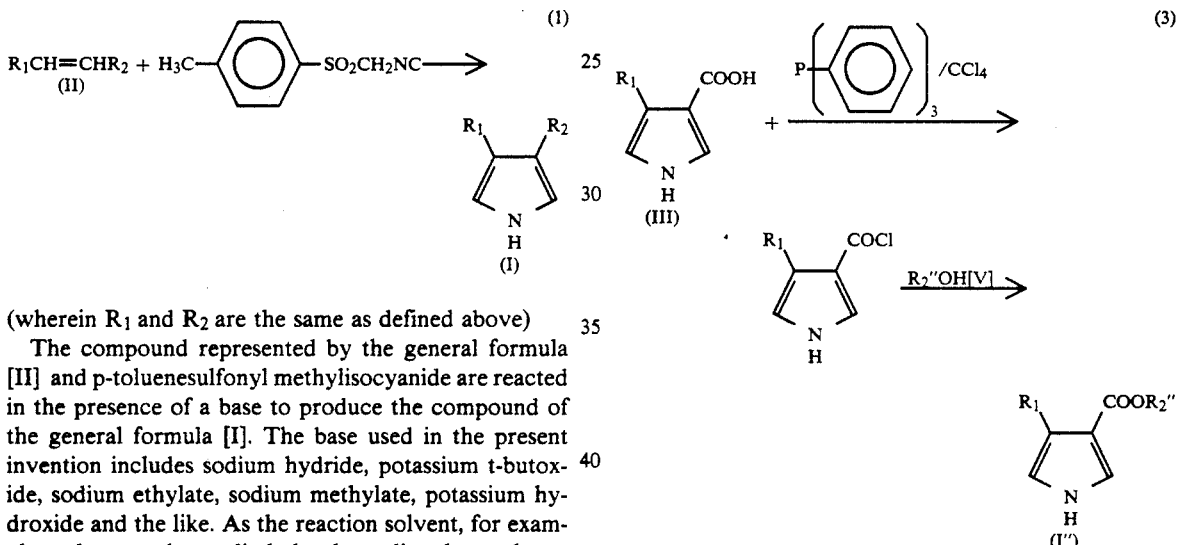

(wherein $R_1$ and $R_2$ are the same as defined above)

The compound represented by the general formula [II] and p-toluenesulfonyl methylisocyanide are reacted in the presence of a base to produce the compound of the general formula [I]. The base used in the present invention includes sodium hydride, potassium t-butoxide, sodium ethylate, sodium methylate, potassium hydroxide and the like. As the reaction solvent, for example, ethers such as diethyl ether, dimethoxyethane, methylene chloride, methanol, ethanol, DMF, DMSO are used alone or a mixture thereof.

The reaction temperature is from $-20°$ C. to the reflux temperature, preferably from $-10°$ to $50°$ C.

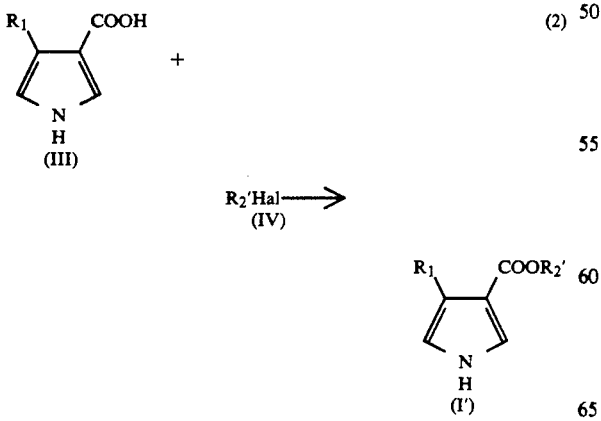

(wherein Hal means halogen, $R_2'$ means a group of the formula:

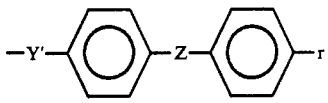

(in which Y' is a direct bond, a branched or a straight chain $C_{1-12}$ alkylene, -alkN($R_8$)-(in which $R_8$ is alkyl) or -alkO— (in which alk is branched or a straight chain $C_{1-12}$ alkylene), $R_1$, Z and r are as defined above.)

The compound represented by the general formula [III] and the compound represented by the general formula [IV] are reacted in the presence of DBU or the like in an nonpolar solvent or acetonitrile to give a product. As the nonpolar solvent, benzene, toluene, xylene and the like can be used. The reaction is carried out at the temperature between room temperature and the reflux temperature. Based on 1 mole of the compound [III], 0.8 to 2 mole of the compound [IV] and 2.0 to 2.4 mole of DBU are used.

{in which $R_2''$ is a group of the formula:

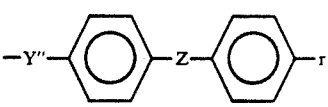

[in which Y" is a direct bond, a branched or a straight chain $C_{1-12}$ alkylene, phenylene or -alkO— (in which alk is a branched or a straight chain $C_{1-12}$ alkylene), $R_1$, Z and r are as defined above]}. The reaction solvent may not be particularly limited as far as it is inert for reagents and reaction products. Generally, acetonitrile, carbon tetrachloride, chloroform, methylene chloride, benzene, toluene, THF, dimethoxyethane and the like may be used. Based on 1 mole of the compound [III], 1.0 to 1.2 mole of triphenylphosphine is used. Based on the compound [III], 1.0 to 3.0 mole of carbon tetrachloride is used unless it is used as solvent. The reaction temperature is from $0°$ C. to $40°$ C. The resulting acid chloride is reacted with the compound [V] in the presence of a base at $0°$ to $50°$ C. without isolation. As such base, triethylamine, pyridine and the like may be used.

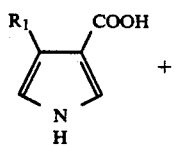

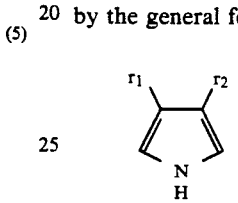

DCC: dicyclohexylcarbodiimide  Py: pyridine
DMAP: 4-dimethylaminopyridine

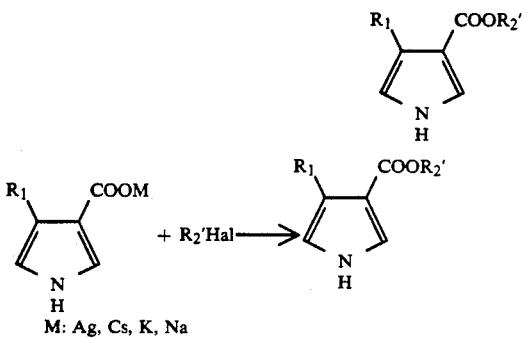

M: Ag, Cs, K, Na

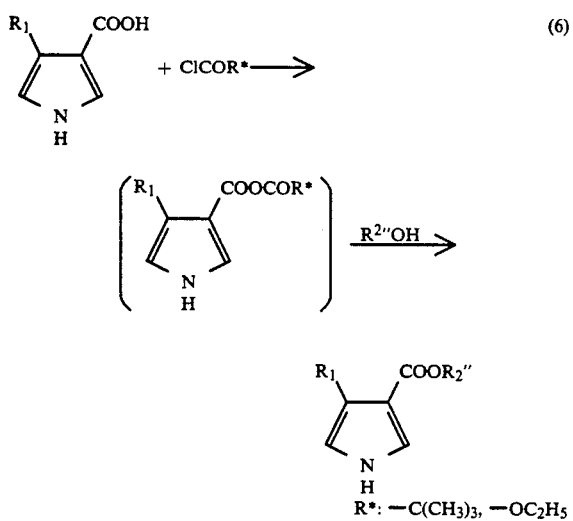

R*: —C(CH$_3$)$_3$, —OC$_2$H$_5$

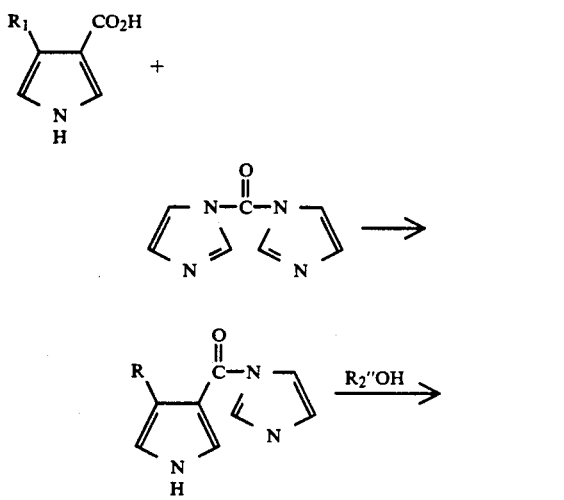

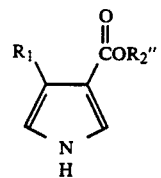

After the reaction is over, the usual work-up is carried out to give the objective product.

The structure of the compound of the present invention was determined by IR, NMR, MS and the like.

Preparation of Conductive Polymer Liquid Crystal Membrane

The pyrrole monomer of the present invention which does not have a unsubstituted or substituted liquid crystal molecule in its side chain a compound represented by the general formula:

(in which r$_1$ and r$_2$ are the same or different and signify hydrogen, an organic substituent such as hydrogen, alkyl, ester, phenyl, benzyl).

In the process for production of the polymer of the compound represented by the general formula [I] by the electropolymerization method of the present invention, the conductive salt is salt of:

(a) at least one cation selected from a group consisting of H$^+$, Li$^+$, Na$^+$, K$^+$, R$^3{}_4$N$^+$, and R$^3{}_4$P$^+$ (in which R$^3$ independently indicates a hydrogen atom, an alkyl group, a cycloalkyl group or an aryl group), and (b) at least one anion selected from a group consisting of BF$_4^-$, AsF$_4^-$, AsF$_6^-$, SbF$_6^-$, SbCl$_6^-$, PF$_6^-$, ClCO$_4^-$, HSO$_4^-$ and SO$_4^{2-}$.

In the above method, 0.001 to 1 Mol/l of the compound of the general formula [I] is added to the solvent dissolving 0.001 to 1 Mol/l of said conductive salt as electrolyte, and direct current is applied, thereby causing polymer to be deposited polymer on the anode, which grows to give a film.

The electrolyte may be any solvent which can dissolve the compound of the general formula [I]. For example, organic solvents such as acetonitrile, benzonitrile, propylene carbonate, dimethylformamide, tetrahydrofuran, nitrobenzene, dichloromethylene, chloroform, dichloroethylene, water or a mixture thereof can be used.

The conductive salt and types of the solvent, applied current, voltage or the like varies depending on the types of the starting compound.

On the other hand, in the process for production of the polymer of the compound represented by the general formula [I] by chemical oxidation process, conventionally used oxidizing agent can be used without particular limitation. For example, the example includes strong oxidizing agent such as Fe$_3^+$ compound, H$_2$O$_2$, S$_2$O$_3{}^2$ compound, Cl$_2$, Br$_2$ and the like; or highly oxidized hydroxy acid ion donor such as RuO$_4^-$ compound, OsO$_4^-$ compound, MnO$_4^-$ compound; or noble metal acid ion donor such as IrCl$_6{}^{2-}$ compound, $PtCl_6^{2-}$ compound, $PdCl_4^{2-}$ compound, $AuCl_4^{2-}$ compound. Particularly, ruthenium (III), tris(vasophenanthrolinesulfonate), ruthenium (III) tris(bipyridinesulphonate) and the like are preferred.

In the chemical oxidation, the reaction may be carried out either in a solvent or non-solvent system, and the polymer is directly obtained as powder or film-like solid.

As the reaction solvent, any solvent which does not react with the oxidizing agent can be used without particular limitation. Preferably, water, lower alcohols, acetonitrile, chloroform or a mixed solvent thereof can be used.

In the reaction in a solvent system, the concentration of the starting compound and the oxidizing agent is not particularly limited. 0.001 Mol/l or a saturated solution can be used to carry out the reaction.

The production of the polymer of the compound represented by the general formula [I] according to the chemical oxidation of the present invention is advantageously conducted by the film-forming method previously disclosed in WO89/01008 (hereinafter referred to as case film-forming method).

The homogeneous and stable solution containing the compound represented by the general formula [I], and oxidizing agent and a solvent to dissolve the said compounds is prepared, which is applied on a base material and the solvent is removed by evaporation to give a polymer membrane.

The summary of the case film-forming method will be described.

Oxidizing agent $FeCl_3$, $CuCl_2$, $Fe(NO_3)_3$, $SbCl_5$, $MoCl_5$, or a hydrate thereof or a mixture thereof. Particularly, $FeCl_3$, $FeCl_3 \cdot 6H_2O$, $Fe(NO_3)_3 \cdot 9H_2O$ are preferred. The amount to be used is 1 to 10 mole based on 1 mole of the above pyrrole derivative. Particularly, 1 to 4 mole is preferred.

Solvent

Aliphatic ethers such as diethyl ether, diisobutyl ether, di-n-butyl ether, diisopropyl ether, dimethoxyethane; cyclic ethers such as THF, dioxane; alcohols such as methanol, ethanol, isopropyl alcohol; halogenated hydrocarbon such as methylene chloride, chloroform, dichloroethane; aromatic hydrocarbon such as benzene, toluene, xylene; aliphatic hydrocarbon such as hexane, heptane; alicyclic hydrocarbon such as cyclohexane; esters such as ethyl acetate, butyl acetate; aliphatic, alicyclic ketones such as acetone, methyl ethyl ketone, methyl isobutyl ketone, cyclohexanone; nitroalkanes such as nitromethane; or a mixed solvent thereof. Particularly, diethylether, methanol, THF, and a mixed solvent thereof are preferred. The amount to be used is 1 to 50 times the volume required to obtain homogeneous solution of the oxidizing agent. Preferably 10 to 30 times the amount is preferred.

Base material

The embodiment of the base material to which the precursor solution of the above polymer in the present invention includes glass pane, metal, polymer film, ceramic plate, glass plate covered with conductive film, fiber, paper, stick, pipe and the like. The surface of such base material may be previously surface-treated using silane coupling agent or the like.

Application of Solvent onto Base Material

As the method to apply the above precursor solution onto the above base material, casting, dipping, spraying, ultrasonic atomization, spin coating method and the like may be employed.

Solvent Flash-off

As the method for removal of solvent, the method wherein the base material on which the solution is applied is maintained at the temperature from about 0° to about 200° C., preferably from room temperature to 100° C. using a hot air dryer, a vacuum constant-temperature dryer or the like may be employed. Alternatively, the method wherein the solution-applied base material is placed on a hot plate and heated in a dust hood, the method wherein heat is applied using an infrared lamp or the like may be employed.

As needed, various treatment methods well known to those skilled in the art, for example, mixing of the polymers of the present invention, mixing the present polymer with other one, addition of various inorganic, organic and metallic additives including a stabilizer, a plasticizer or the like may be employed.

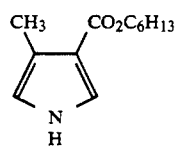

Figure 1:
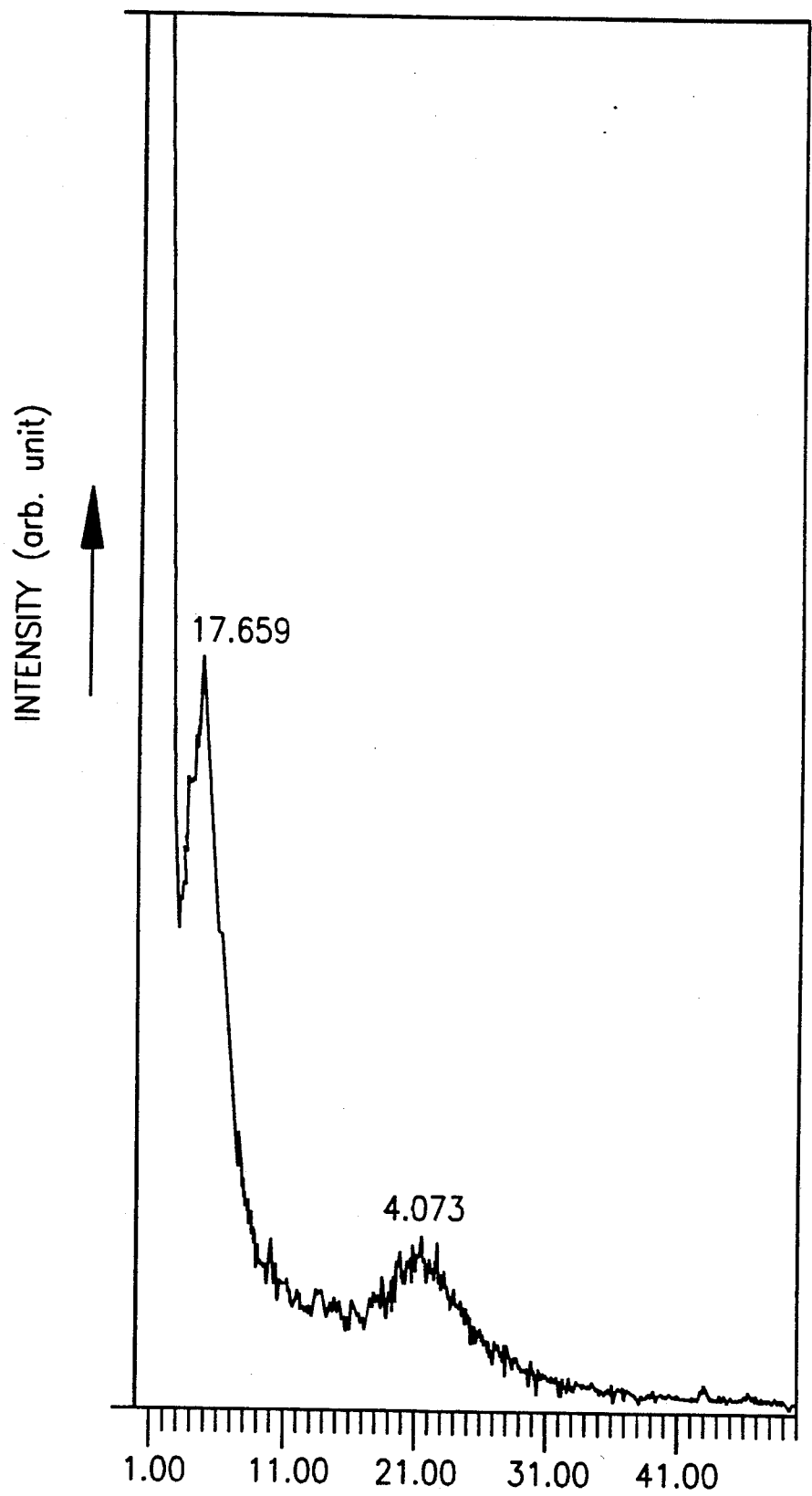
FIGS. 1 and 3 are charts of X-ray diffraction and DSC of the polymer film obtained from the compound.
Figure 2:
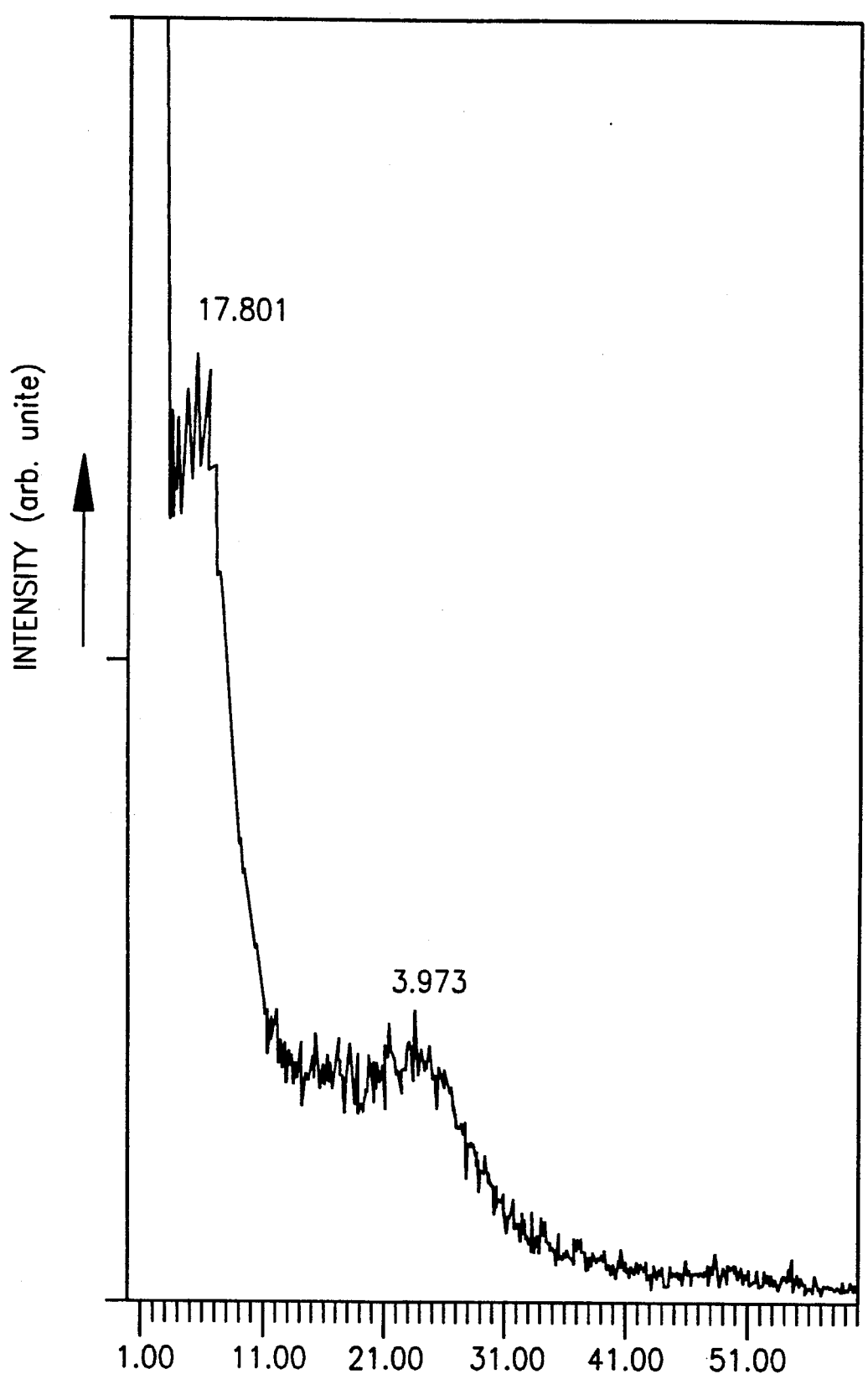
Figure 3:
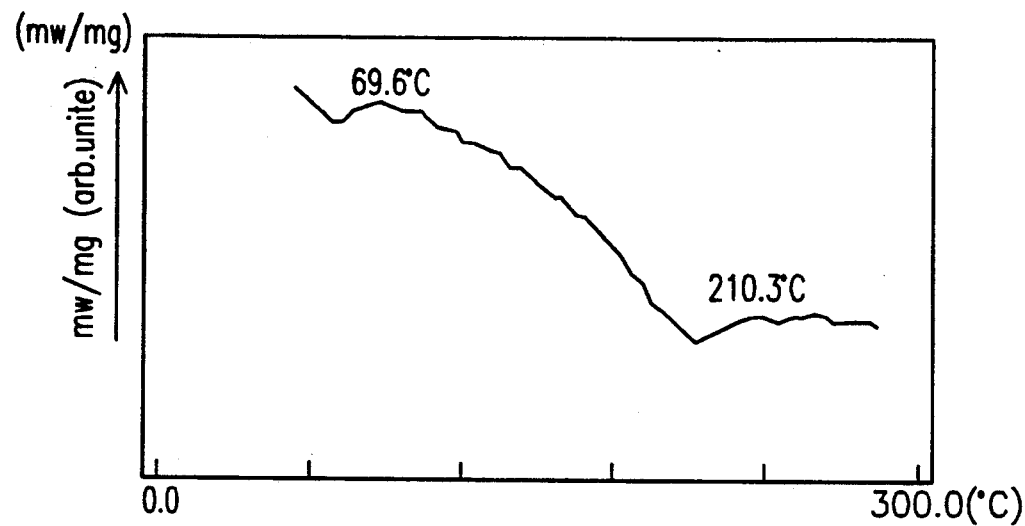
Figure 4:
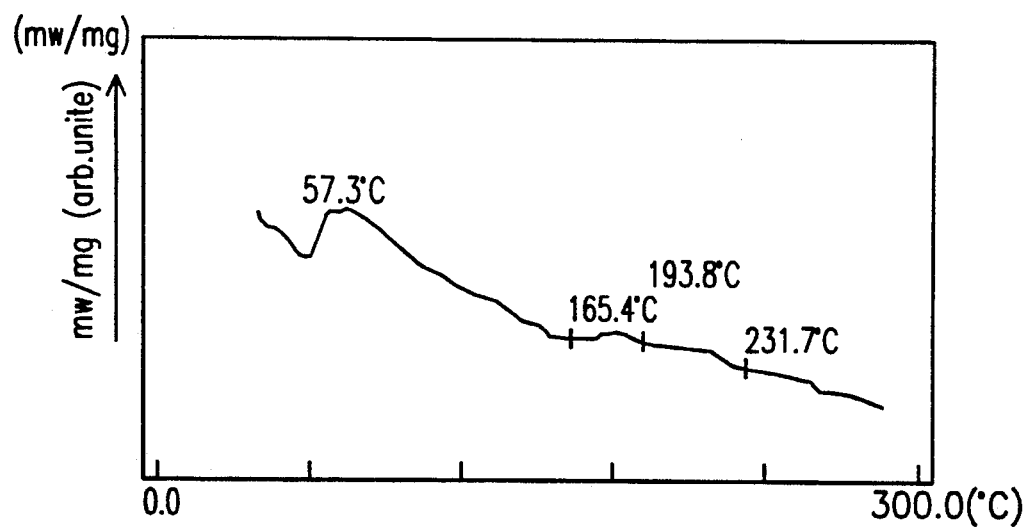

FIGS. 2 and 4 are X-ray diffraction and DSC charts of the polymer film of Example 4;

FIGS. 5, 6, 7 and 10 are DSC charts of Examples 5, 6, 7 and 11, respectively.

Figure 8:
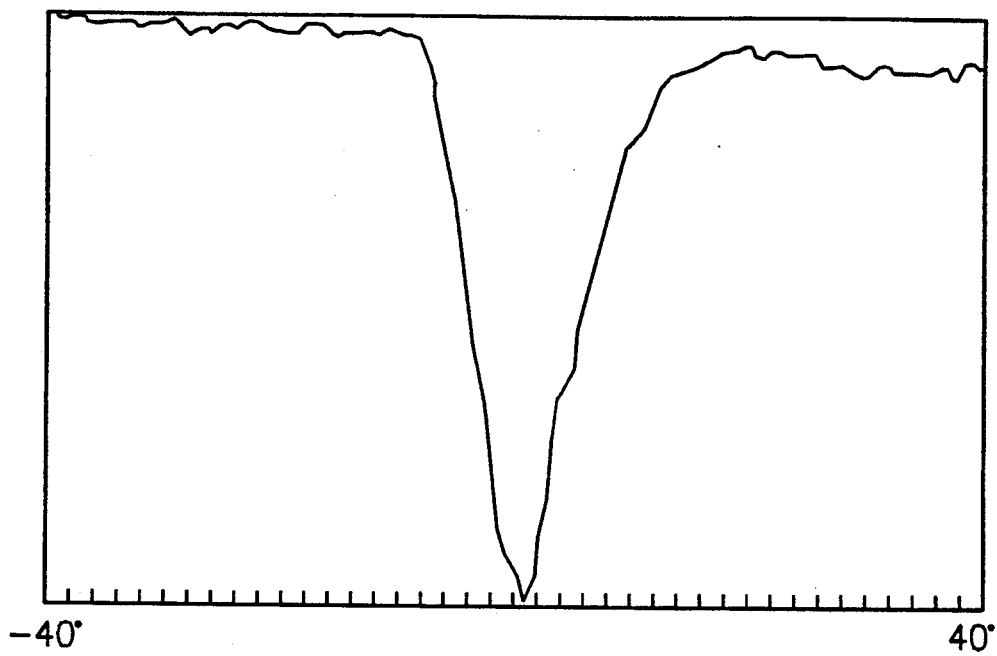
Figure 9:
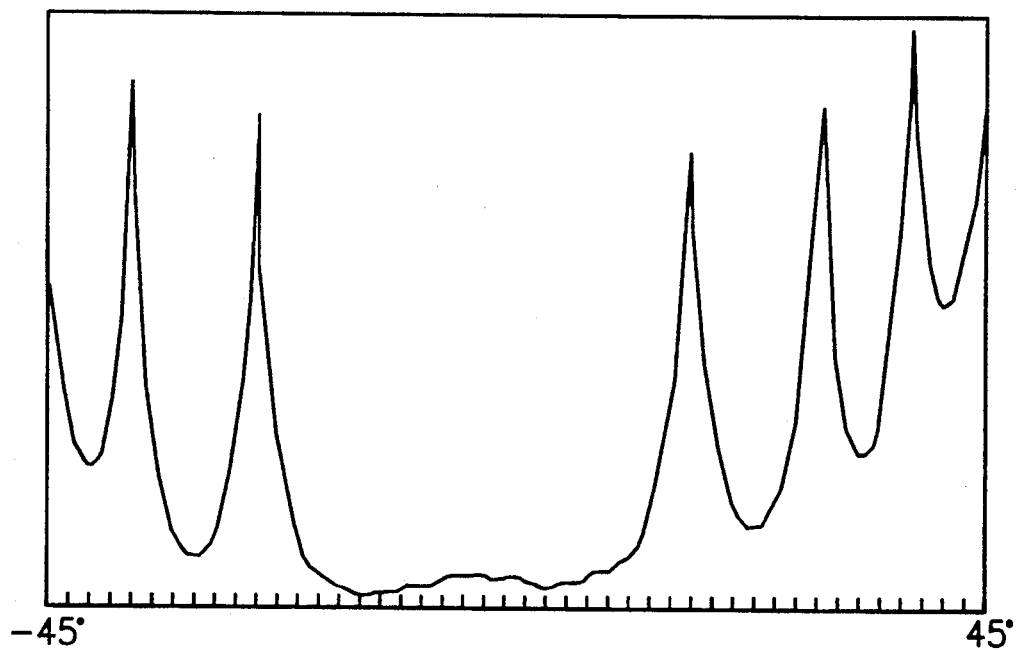

FIGS. 8 and 9 are charts of the film of Example 5 and a quartz plate determined using a non-linear optical material evaluation tester.

DESCRIPTION OF THE PREFERRED EMBODIMENTS

The present invention will be further explained in detail in the following examples.

EXAMPLE 1

Methyl 4-{4-[4-(4-cyanophenyl)phenoxy]n-buthyl}-3-pyrrole carboxylate (Compound No. 1)

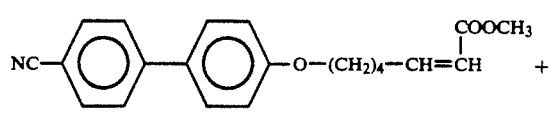

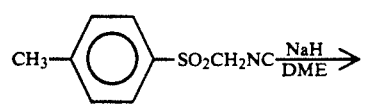

-continued

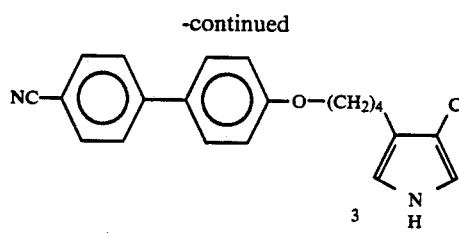

The compound represented by the formula 1 (3.35 g, 0.01 mol) was dissolved in DME (dimethoxyethane) (15 ml), to which was added the compound represented by the formula 2 (2.05 g, 0.0105 mol) to give a homogeneous solution. DME (10 ml) and 60% NaH (in oil) (0.015 mol) were added and the resultant was added to a curved-neck flask equipped with a stirrer, a condenser, a thermometer and a dropping funnel. The above solution of the compounds 1 and 2 was dropped in small portions from the dropping funnel into the above flask.

Immediately, hydrogen gas was observed to generate and the reaction temperature increased. The reaction temperature was controlled at 0° to 5° C. using an ice/water bath. After dropping was over, the product was matured at the same temperature for an hour and the reaction was concluded.

The reaction solution was treated according to the conventional methods, purified by column chromatography, and identified by IR, NMR, MASS spectra. Yield was 75%, m.p.: 137°–138° C.

EXAMPLE 2

5-[4-(4-Cyanophenyl)phenoxy]n-pentyl 4-methyl-3-pyrrole carboxylate ester (Compound No. 2):

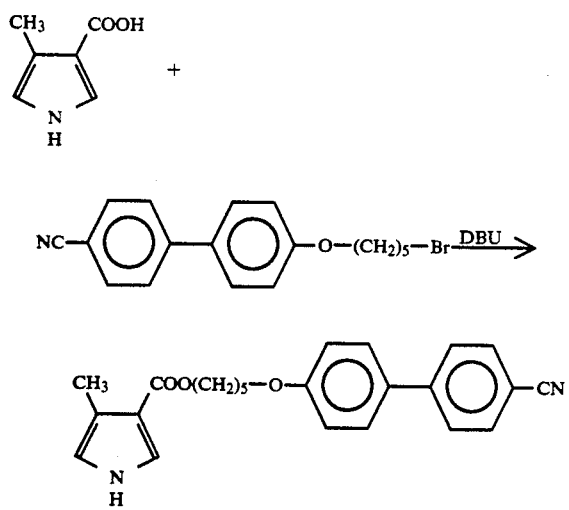

4-Methyl-3-pyrrole carboxylic acid (5.86 g, 46.9 mmol), 4-[4-(5-brom-n-pentyloxy)phenyl]benzonitrile (14.65 g, 42.6 mmol) and DBU (15.7 g, 103.3 mmol) were added to benzene (100 ml), which was heated and refluxed for an hour. After the reaction was over, the reaction solution was cooled, to which was added water, and the resultant was extracted with ethyl acetate. The ethyl acetate layer was washed with water, dried over anhydrous magnesium sulfate, then the solvent was distilled off under reduced pressure. The residue was recrystallized from benzene to give the objective product (9.5 g). Yield: 57.4%, m.p.: 151°–153° C.

EXAMPLE 3

4-Phenylazophenyl 4-methyl-3-pyrrole carboxylate ester (Compound No. 6):

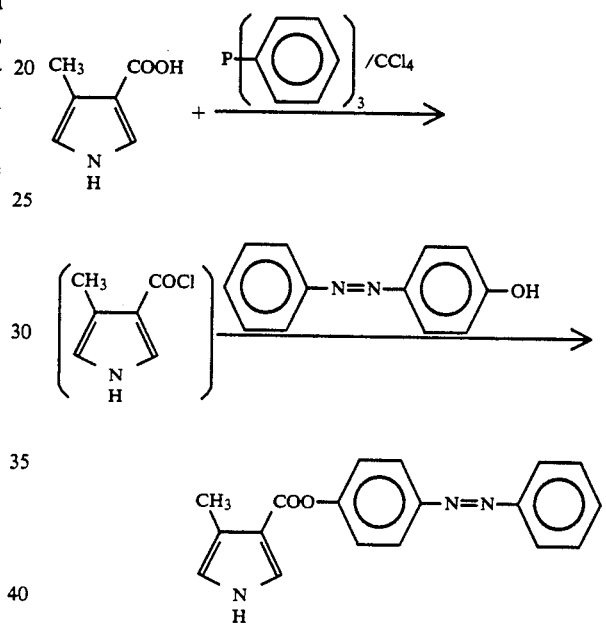

4-Methyl-3-pyrrolecarboxylic acid (3.75 g, 30 mmol) was dissolved in acetonitrile (40 ml), to which was added triphenylphosphine (8.66 g, 33 mmol) at room temperature, followed by carbon tetrachloride (10.2 g, 66 mmol). After the reaction for 2 hours, the solution was added to a solution of 4-hydroxyazobenzene (5.94 g, 30 mmol) and triethylamine (3.3 g, 33 mmol) in acetonitrile (30 ml) at 10° C. After the reaction was over, the reaction solution was poured into water, extracted with ethyl acetate, and the ethyl acetate layer was washed with dilute aqueous solution of sodium hydroxide and water.

After drying over anhydrous magnesium sulfate, the solvent was distilled off and the residue was recrystallized from methanol to give the objective product (4.5 g). Yield: 49.1%, m.p.: 206°–207° C.

The typical examples of the compound of the present invention including the above examples are shown in Table 1.

Some of the present compounds (monomers) exhibit liquid crystal properties.

TABLE 1

Structural Formula:

R1, R2 substituted on pyrrole (N-H)

| Compound Nos. | R$_1$ | R$_2$ | Physical Constants [ ] m.p. °C. |
|---|---|---|---|
| 1 | H$_3$COOC | —(CH$_2$)$_4$O—⟨C$_6$H$_4$⟩—⟨C$_6$H$_4$⟩—CN | [137–138] |
| 2 | CH$_3$ | —COO(CH$_2$)$_5$O—⟨C$_6$H$_4$⟩—⟨C$_6$H$_4$⟩—CN | [151–153] |
| 3 | CH$_3$ | —COO(CH$_2$)$_5$O—⟨C$_6$H$_4$⟩—N=N—⟨C$_6$H$_5$⟩ | [127–127.5] |
| 4 | CH$_3$ | —COO(CH$_2$)$_{12}$O—⟨C$_6$H$_4$⟩—⟨C$_6$H$_4$⟩—CN | [80–82] |
| 5 | CH$_3$ | —COO(CH$_2$)$_5$O—⟨C$_6$H$_4$⟩—COO—⟨C$_6$H$_4$⟩—CN | — |
| 6 | CH$_3$ | —COO—⟨C$_6$H$_4$⟩—N=N—⟨C$_6$H$_5$⟩ | [206–207] |
| 7 | CH$_3$ | —COO—⟨C$_6$H$_4$⟩—⟨C$_6$H$_4$⟩—CN | [278–280] |
| 8 | CH$_3$ | —COO(CH$_2$)$_5$O—⟨C$_6$H$_4$⟩—⟨C$_6$H$_4$⟩—NO$_2$ | [146–147] |
| 9 | CH$_3$ | —COO(CH$_2$)$_{12}$O—⟨C$_6$H$_4$⟩—⟨C$_6$H$_4$⟩—NO$_2$ | [92.5–93] |
| 10 | CH$_3$ | —COO(CH$_2$)$_5$O—⟨C$_6$H$_4$⟩—N=N—⟨C$_6$H$_4$⟩—NO$_2$ | [177.5–178] |
| 11 | CH$_3$ | —COO(CH$_2$)$_5$O—⟨C$_6$H$_4$⟩—CH=NNH—⟨C$_6$H$_4$⟩—NO$_2$ | [197.5–198] |
| 12 | CH$_3$ | —COO(CH$_2$)$_5$O—⟨C$_6$H$_4$⟩—S—⟨C$_6$H$_4$⟩—NO$_2$ | [86–87] |

TABLE 1-continued

Structural Formula $$\underset{\underset{H}{N}}{\overset{R_1 \quad R_2}{\text{pyrrole}}}$$

| Compound Nos. | $R_1$ | $R_2$ | Physical Constants [ ] m.p. °C. |
|---|---|---|---|
| 13 | $CH_3$ | $-COO(CH_2)_5O-\bigcirc-CH=CH-\bigcirc-NO_2$ | [162–163] |
| 14 | $CH_3$ | $-COO(CH_2)_5O-\underset{CH_3}{\bigcirc}-CH=CH-\bigcirc-NO_2$ | [164–165] |
| 15 | $H_3COOC-$ | $-(CH_2)_6O-\bigcirc-\bigcirc-NO_2$ | [175–176] |
| 16 | $CH_3$ | $-COO(CH_2)_6O-\bigcirc-COO-\bigcirc-OC_4H_9$ | [100.5–101] |
| 17 | $CH_3$ | $-COO(CH_2)_{12}O-\bigcirc-COO-\bigcirc-OC_4H_9$ | [78–79] |
| 18 | $CH_3$ | $-COO(CH_2)_6O-\bigcirc-COO-\bigcirc-O\overset{O}{\overset{\|}{C}}-C_4H_9^S$ | [72–73] |
| 19 | $CH_3$ | $-COO(CH_2)_{12}O-\bigcirc-COO-\bigcirc-O\overset{O}{\overset{\|}{C}}-C_4H_9^S$ | [58–59] |
| 20 | $CH_3$ | $-COO(CH_2)_{12}O-\bigcirc-COO-\bigcirc-OC_8H_{17}$ | [74–75] |
| 21 | $CH_3$ | $-COO(CH_2)_6O-\bigcirc-COO-\bigcirc-F$ | $n_D^{25.5}$ 1.5537 |
| 22 | $CH_3$ | $-COO(CH_2)_{12}O-\bigcirc-COO-\bigcirc-F$ | [64–65] |

EXAMPLE 4

The compounds:

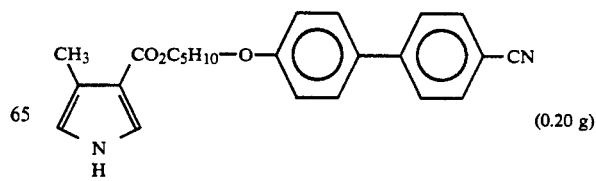

(0.20 g)

-continued

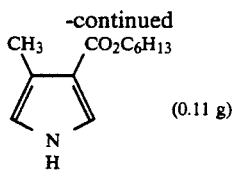

(0.11 g)

were added to a solution of anhydrous FeCl$_3$ (0.47 g) in 1,2-dichloroethane/CH$_3$OH (8/2(vol)) (10 ml). The solution was poured onto a glass plate on a hot plate (40° C.), and the solvent was removed under reduced pressure. Removal of the solvent and polymerization were simultaneously conducted and black film was obtained on the glass plate.

The film was washed with MeOH, H$_2$O, and after drying, a red brown film of 1 μm thickness was obtained.

This film was subjected to doping in I$_2$ atmosphere for 2 hours, then the electrical conductivity of the film was determined by four terminal method (Rollesta Ap, manufactured by Mitsubishi Yuka). The result was $4.0 \times 10^{-1}$ S/cm.

X-ray Diffraction and DSC measurement of the film were conducted. As the result, the polymer exhibited liquid crystal properties (Cf. FIGS. 2 and 4).

Thus, polymer thin layer having electrical conductivity and liquid crystal property was obtained.

EXAMPLE 5

The compound:

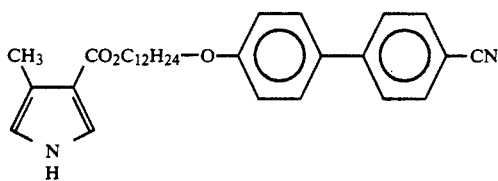

Figure 5:
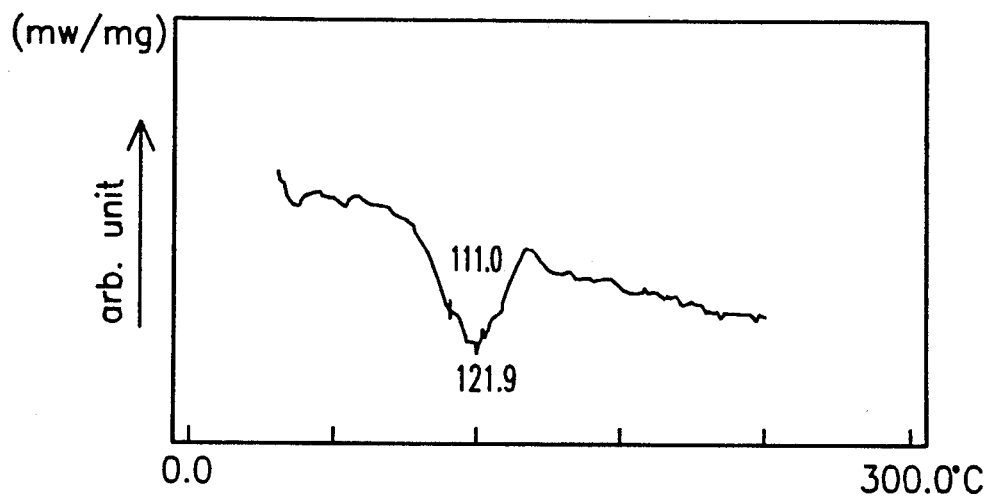

(0.497 g, 1 mmol) was added to FeCl$_3$ (0.487 g, 3 mmol) in 1,2-dichloroethane/methanol solution mixture (ratio 4:1(by volume), 10 ml), which was cast on a glass plate heated to 40° C. The solvent was evaporated under reduced pressure to give a polymerized film. The polymerized film was sufficiently washed with methanol and dried to give a soft and self-maintainable film. The film exhibited liquid crystal property. DSC chart is shown in FIG. 5. The conductivity of the film upon doping with I$_2$ was 1.8 S/cm.

Subsequently, the above film was heated at 150° C., stretched by 1.2-1.3 times, and determined by a non-linear optical material evaluation tester (manufactured by Tokyo Instrument).

The light source was YAG laser ($\omega = 1.06$ μm), and the modulated light was measured using a photoelectric tube ($\omega/2 = 532$ nm).

The result is shown in FIG. 8. FIG. 9 shows the result using a quartz plate as a subject.

FIG. 8 shows that the above film exhibits the function as a secondary non-linear optical material. According to the determination of tertiary non-linear modulation, light modulated to $\omega/3 = 355$ nm was observed.

EXAMPLE 6

The compound:

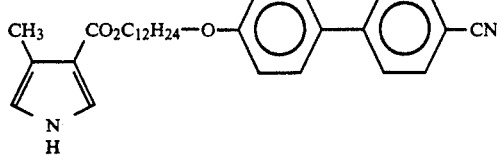

Figure 6:
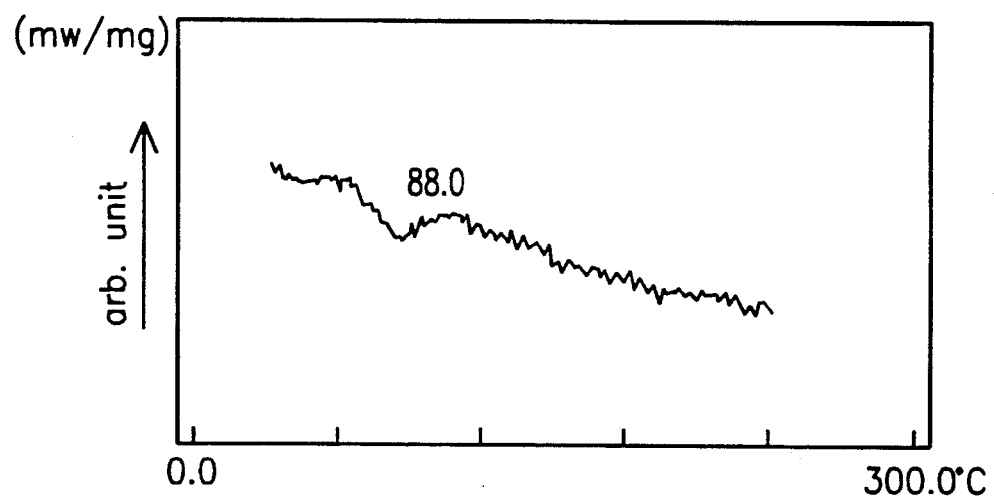

(0.243 g, 0.5 mmol) and the compound:

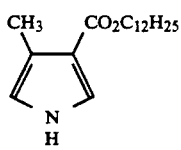

were added to FeCl$_3$ (0.487 g, 3 mmol) in 1,2-dichloroethane/methanol solution mixture (4:1 (by volume), 10 ml) and the resultant was polymerized in the same manner to give a self-maintainable film. The conductivity of the film was 2.4 S/cm. DSC chart is shown in FIG. 6.

EXAMPLE 7

The compound:

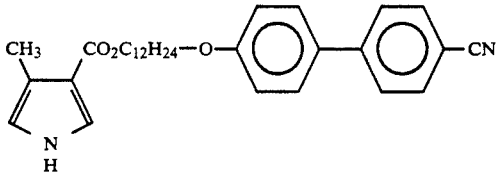

(0.243 g, 0.5 mmol) and the compound:

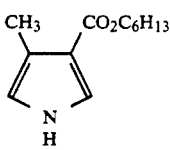

Figure 7:
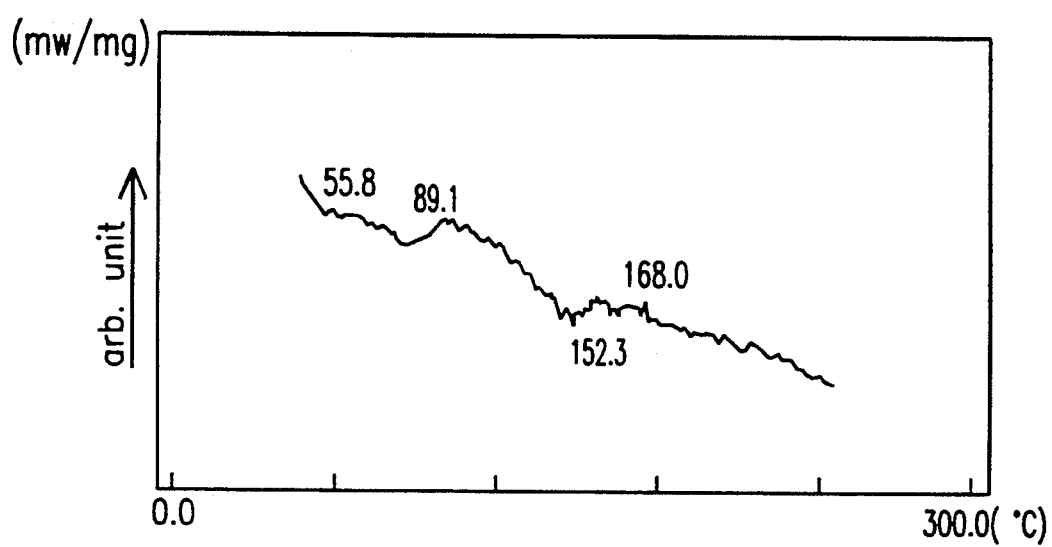

(0.105 g, 0.5 mmol) were dissolved in FeCl$_3$ (0.487 g, 3 mmol) in 1,2-dichloroethane/methanol solution mixture (4:1 (by volume), 10 ml), and the resultant was polymerized in the same manner to give a self-maintainable film. The conductivity of the film after doping with I$_2$ was 0.47 S/cm. DSC chart is shown in FIG. 7.

EXAMPLE 8

The compound:

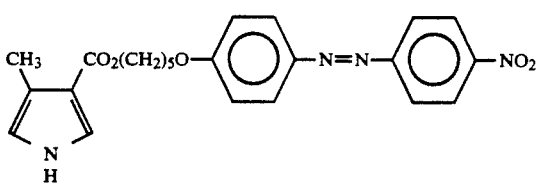

(0.436 g) was added to FeCl$_3$ (1.45 g) in 1,2-dichloroethane/methanol solution mixture (4:1 (by volume), 30 ml). The mixed solution was poured into a gill jar equipped with a glass plate which can be heated, to give a film. Polymerization was carried out at 40° C. while the solvent was removed under reduced pressure, to give a film. The polymerized film was sufficiently washed with methanol and dried. The film was subjected to doping in $I_2$ atmosphere and whose conductivity was measured with four probe technique. The result was $1.7 \times 10^{-1}$ S/cm. According to DSC analysis of the film, the polymerized film exhibited liquid crystal property.

EXAMPLE 9

The procedure of Example 8 was repeated except that the compound:

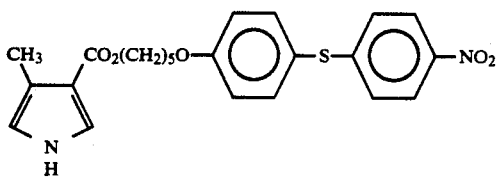

(0.44 g), $FeCl_3$ (0.48 g) and 1,2-dichloroethane/methanol solution mixture (4:1 (by volume), 10 ml) were used to give a polymer film having conductivity ($3.5 \times 10^{-2}$ S/cm ($I_2$)) and liquid crystal property.

EXAMPLE 10

The procedure of Example 8 was repeated except that the compound:

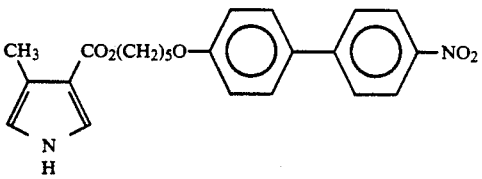

(0.408 g) was used to give a polymer film having conductivity ($6.3 \times 10^{-1}$ S/cm ($I_2$)) and liquid crystal property.

EXAMPLE 11

The procedure of Example 8 was repeated except that the compound:

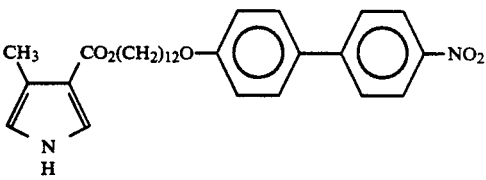

Figure 10:
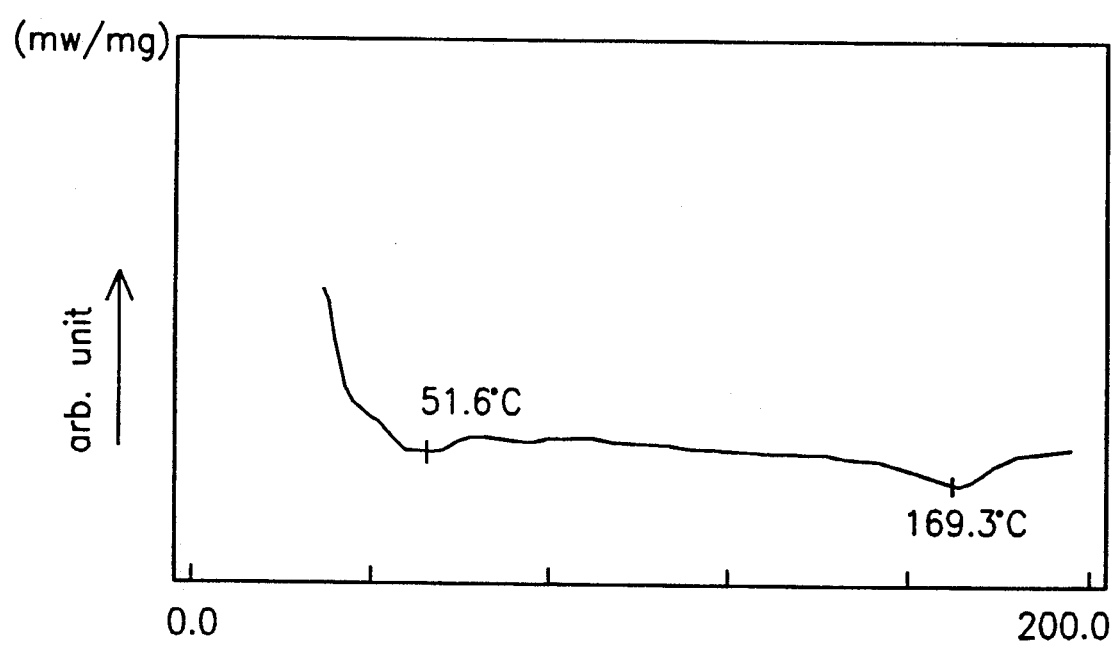

(0.06 g), $FeCl_3$ (0.12 g) and 1,2-dichloroethane/methanol solution mixture (4:1 (by volume), 25 ml) were used to give a polymer film having conductivity ($1.7 \times 10^{-2}$ S/cm ($I_2$)) and liquid crystal property. The DSC chart of the film is shown in FIG. 10.

EXAMPLE 12

The procedure of Example 8 was repeated except that the compound:

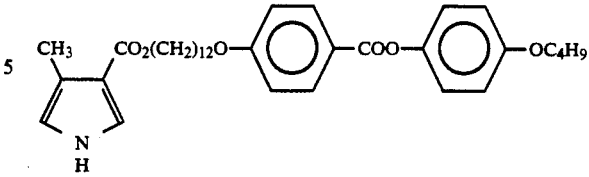

(0.577 g), $FeCl_3$ (0.48 g) and 1,2-dichloroethane/methanol solution mixture (4:1 (by volume), 10 ml) were used, to give a polymer film having conductivity ($7.5 \times 10^{-2}$ S/cm ($I_2$)) and liquid crystal property. The film was heated to 150° C. and stretched by 1.5 times (the oriented film became a clear yellow film compared with the film before orientation). The film was placed and observed under a polarization microscope with temperature control. As the result, reversible change in color of polarized light depending on temperature having a threshold value around 95° C. was observed.

Observation under polarization:

$$\text{yellow} \underset{}{\overset{95° C.}{\rightleftarrows}} \text{bluish green}$$

Observation under non-polarization:

$$\text{yellow} \underset{}{\overset{95° C.}{\rightleftarrows}} \text{yellow}$$

AVAILABILITY IN INDUSTRIAL APPLICATION

The compound of the present invention can be advantageously produced by an industrial process, and the polymer membrane according to the present invention can convert various functions of liquid crystal molecules into electrical signals. Thus the present invention can provide novel composite functional materials. The conductive polymer liquid crystal film of the present invention can be applied to opto-electronics, particularly, electron-photone interchanger such as display device of, for example, electronic calculator, watches, clocks, electronic optical shutter, electronic optical condenser, optical modulator, optical communication path transfer switch, memory, liquid crystal printer head.

What is claimed is:

1. A compound of formula

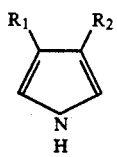

wherein $R_1$ is hydrogen, cyano, alkyl, phenyl, benzyl, —$COR_3$, wherein $R_3$ is alkyl, phenyl, benzyl, or —$COOR_4$ wherein $R_4$ is hydrogen, alkyl, phenyl, benzyl, $R_2$ is

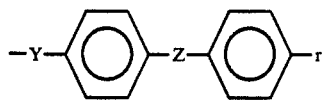

wherein
Y is a direct bond, branched or straight-chain $C_1$-$C_{12}$ alkylene, phenylene, —CO—, —COO—, COOalk, —COOalkO—, —COOalk N($R_8$) wherein $R_8$ is alkyl, or —alkO wherein alk, each instance, is a branched or straight-chain $C_1$-$C_{12}$ alkylene, Z is —HC=CH—, —CH=NNH—, —N=N(O)—, —C≡C—, —COO—, —N=N—, —S—, or a direct bond, r is hydrogen, nitro, cyano, halogen, alkyl or alkoxy having zero or one asymmetric carbon, —$COR_5$ wherein $R_5$ is an alkyl having zero or one asymmetric carbon, phenyl, —$COOR_6$, or —$OCOR_7$ wherein $R_6$ and $R_7$ are each independent of the other hydrogen, an alkyl having zero or one asymmetric carbon, phenyl, with the proviso that $R_1$ or $R_2$ or $R_1$ and $R_2$ each is an electron attractive group.

2. Methyl 4-{4-[4-(4-cyanophenyl)phenoxy]n-butyl}-3-pyrrole carboxylate.

3. 5-[4-(4-cyanophenyl)phenoxy]n-pentyl-4-methyl-3-pyrrole carboxylate ester.

4. 4-phenylazophenyl-4-methyl-3-pyrrole carboxylate ester.

5. Pyrrole monomer comprising the reaction product of:
A) compound of the formula $R_1CH=CHR_2$ wherein
$R_1$ is hydrogen, cyano, alkyl, phenyl, —$COR_3$, wherein $R_3$ is alkyl, phenyl, benzyl, or —$COOR_4$ wherein $R_4$ is hydrogen, alkyl, phenyl, benzyl,
$R_2$ is

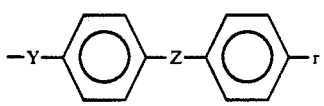

wherein
Y is a direct bond, branched or straight-chain $C_1$-$C_{12}$ alkylene, phenylene, —CO—, —COO—, —COOalk, —COOalkO—, —COOalkN($R_8$) wherein $R_8$ is alkyl, or —alkO, wherein alk, each instance, is a branched or straight-chain $C_1$-$C_{12}$ alkylene,
Z is —HC=CH—, —CH=NNH—, —N=N(O)—, —C≡C—, —COO—, —N=N—, —S—, or a direct bond,
r is hydrogen, nitro, cyano, halogen, alkyl or alkoxy having zero or one asymmetric carbon, —$COR_5$ wherein $R_5$ is an alkyl having zero or one asymmetric carbon, phenyl, —$COOR_6$, or —$OCOR_7$ wherein $R_6$ and $R_7$ are each independent of the other hydrogen, an alkyl having zero or one asymmetric carbon, phenyl,
with the proviso that $R_1$ or $R_2$, or $R_1$ and $R_2$ each is an electron attractive group, and,
B) compound of the formula

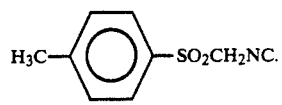

6. Pyrrole monomer comprising the reaction product of:
A) compound of the formula

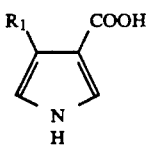

$R_1$ is hydrogen, cyano, alkyl, phenyl, benzyl, —$COR_3$, wherein $R_3$ is alkyl, phenyl, benzyl, or —$COOR_4$ wherein $R_4$ is hydrogen, alkyl, phenyl, benzyl,
and,
B) compound of the formula $R'_2$ Hal
wherein
$R'_2$ is

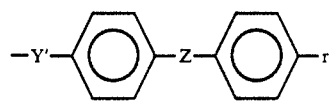

wherein
Y' is a direct bond, branched or straight-chain $C_1$-$C_{12}$ alkylene, -alk N($R_8$)—, wherein $R_8$ is alkyl, or —alkO—, wherein alk is branched or straight-chain $C_1$-$C_{12}$ alkylene,
Z is —HC=CH—, —CH=NNH—, —N=N(O)—, —C≡C—, —COO—, —N=N—, —S—, or a direct bond,
r is hydrogen, nitro, cyano, halogen, alkyl or alkoxy having zero or one asymmetric carbon, —$COR_5$ wherein $R_5$ is an alkyl having zero or one asymmetric carbon, phenyl, —$COOR_6$, or —$OCOR_7$, wherein $R_6$ and $R_7$ are each independent of the other hydrogen, an alkyl having zero or one asymmetric carbon, phenyl,
with the proviso that $R_1$ or $R'_2$, or $R_1$ and $R'_2$ each is an electron attractive group, and,
Hal is halogen.

7. Pyrrole monomer comprising the reaction product of:
A) compound of the formula

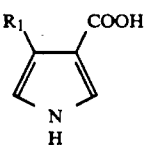

wherein
$R_1$ is hydrogen, cyano, alkyl, phenyl, benzyl, —$COR_3$, wherein $R_3$ is alkyl, phenyl, benzyl, or —$COOR_4$ wherein $R_4$ is hydrogen, alkyl, phenyl, benzyl,
in the presence of reactive compound

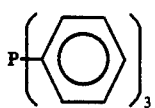

and carbon tetrachloride, and,

B) compound of the formula

R''₂OH wherein

R''₂ is 

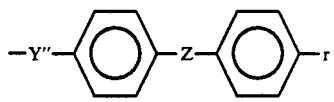

wherein

Y'' is a direct bond, branched or straight-chain, $C_1$-$C_{12}$ alkylene, phenylene, or —alkO— wherein alk is branched or straight-chain $C_1$-$C_{12}$ alkylene, Z is —HC=CH'—, —'CH=NNH—, —N=N(O)—, —C≡C—, —COO—, —N=N—, —S—, or a direct bond, r is hydrogen, nitro, cyano, halogen alkyl or alkoxy having zero or one asymmetric carbon, —COR₅ wherein R₅ is an alkyl having zero or one asymmetric carbon, phenyl, —COOR₆, or —OCOR₇ wherein R₆ and R₇ are each independent of the other hydrogen, alkyl having zero or one asymmetric carbon, phenyl, with the proviso that R₁ or R''₂, or R₁ and R''₂ each is an electron attractive group.

* * * * *